United States Patent [19]
Stenger et al.

[11] 3,940,490
[45] Feb. 24, 1976

[54] MEDICAMENTS HAVING PSYCHOTROPIC PROPERTIES

[75] Inventors: M. Antoine Stenger; Henri Cousse; M. Gilbert Mouzin, all of Castres, France

[73] Assignee: Pierre Fabre S.A., Castres, France

[22] Filed: Nov. 21, 1974

[21] Appl. No.: 525,951

Related U.S. Application Data

[63] Continuation of Ser. No. 264,501, June 20, 1972.

[30] Foreign Application Priority Data
June 21, 1971 France .............................. 71.22575
June 5, 1972 France .............................. 72.20391

[52] U.S. Cl. ............................ 424/230; 260/559 S
[51] Int. Cl.$^2$ ...................................... A61K 31/165
[58] Field of Search .................... 260/559; 424/324

[56] References Cited
UNITED STATES PATENTS
2,848,418   8/1958   Müller et al. ...................... 252/51.5

Primary Examiner—Stanley J. Friedman
Attorney, Agent, or Firm—Gordon W. Hueschen

[57] ABSTRACT

N—$C_1$ to $C_4$-alkyl-5-bromo-ortho-cresotamides; their use as anticonvulsants. 5-Bromo-ortho-cresotamide may also be named 5-Bromo-2-hydroxy-3-methyl-benzamide.

4 Claims, No Drawings

MEDICAMENTS HAVING PSYCHOTROPIC PROPERTIES

This is a continuation of application Ser. No. 264,501, filed June 20, 1972.

The present invention relates to a series of derivatives having psychotropic activities which are derived from cresotic acid.

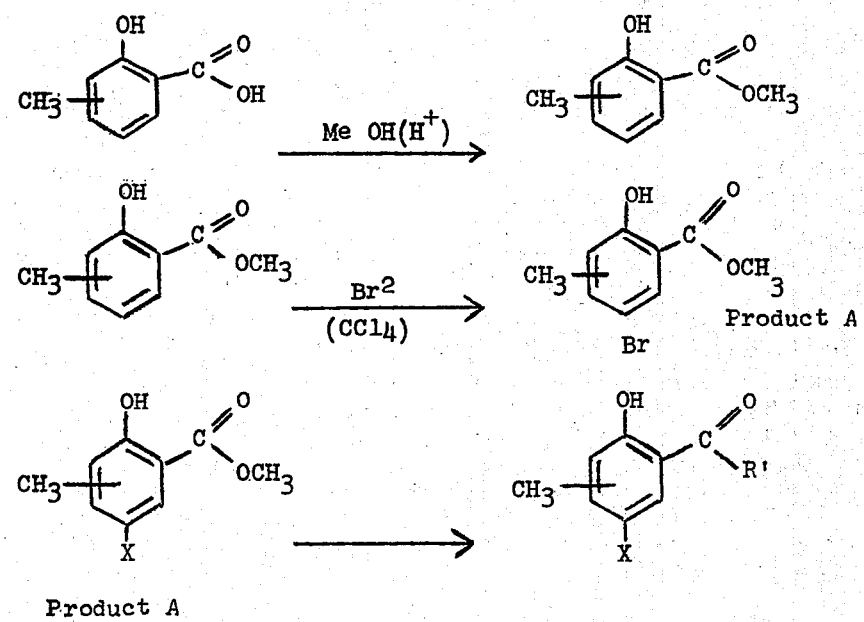

These new drugs have the overall formula:

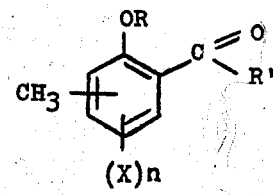

R may be a hydrogen, a straight or branched-chain lower alkyl radical, an alkenyl radical, an ethinyl radical, or an esterifying acid radical, namely acyl, thenoyl, halothenoyl or benzoyl.

R' may be an —OH, —OCH₃, —O-alkyl, O-alkenyl, O-ethinyl, —NH₂, straight or branched-chain N—dialkyl, —NH-alkyl, NR''—A—N-dialkyl, —O—A—N-dialkyl, NR''—A—N-morpholino, or —N-cycloalkyl radical.

A may be a straight or branched alkyl chain of 2 to 5 carbon atoms, which chain may be unsaturated.

R'' may be a hydrogen or a lower alkyl.

Finally, the nitrogen atom may be included in a ring to form a piperidino, pyrrolidono, morpholino or piperazino group, for example:

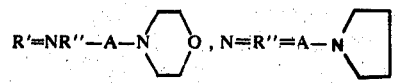

X may be a hydrogen, halogen or an NO₂ radical.

n may be equal to 0, 1 or 2.

The position of the CH₃ radical on the ring may vary.

The invention also relates to therapeutically acceptable salts of derivatives having an amine function.

These derivatives may be obtained by different methods, namely:

METHOD A (Aminolysis of the Corresponding Methyl Ester)

Principle:

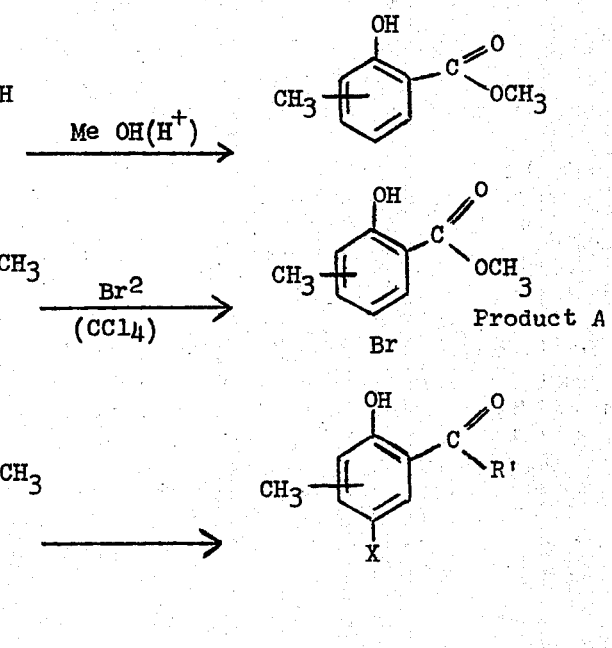

To 1 mol of Product A 1.5 mol of the corresponding amine is added. When the amine is gaseous it is used in alcoholic solution and the reaction can be carried out in an autoclave.

When the amine is crystalline, a solvent is employed; on the other hand, when it is liquid, we did not employ a solvent.

The reaction mixture is set aside for several hours at room temperature and then heated for a few hours at 90°C. The solvent, if any, is distilled and the products are recovered by the customary techniques, namely:

distillation under reduced pressure, or crystallization of the amide.

In the case of diamines, the products can be recovered in the form of hydrochloride.

EXAMPLES

Preparation of methyl 5-bromo 2-hydroxy 3-methyl benzoate

Add 300 g of cresotic acid to a solution of 90 g of sulfuric acid in anhydrous methanol; heat for 30 hours; the solution becomes dark red. Expel the methanol, dissolve the residue in chloroform and pour into ice water; the original cresotic acid crystallizes and can be removed. The chloroform phase is washed with a bicarbonate solution in water, dried over Na₂SO₄ and concentrated and the residue distilled. (b.p.₁₅ = 104°–105°C). Methyl 2-hydroxy 3-methyl benzoate is obtained; the yield is 77%. The index of refraction $n_D^{25}$ is equal to 1.5322.

Silica plate chromatography.
Solvent: ethyl acetate/petroleum ether (5:95)
$R_f$: 0.72.

The methyl 2-hydroxy 3-methyl benzoate in solution in the dioxane is added, drop by drop, to a chloroform solution of bromine maintained at 0°C. Excess bromine can be used since only one position is capable of bromination in the event that the methyl group is in 3 position.

Then set aside for several hours under nitrogen, recover the chloroform phase, wash with a bicarbonate solution and then with water, concentrate, and crystallize.

This product is obtained in the form of fine white needles.

Melting point: 107°C.
Soluble in dimethyl formamide, dimethyl acetamide, methyl pyrrolidone, ether, and chlorinated solvents.

Preparation of 5-bromo 2-hydroxy 3-methyl benzamide

Add 900 cc of 20% ammonia to 49 g of methyl 5-bromo 2-hydroxy 3-methyl benzoate in 2 liters of ethanol at 95°C. Set aside for 72 hours at room temperature, with agitation; cool with ice, add 300 cc of hydrochloric acid (6N), and then extract with ether; finally concentrate and crystallize by addition of petroleum ether; 29 g of 5-bromo 2-hydroxy 3-methyl benzamide are obtained (yield: 63%).

to distillation under vacuum (b.p.: 100°C at 5 mm Hg). 944 g of methyl ester (I) are obtained (yield 90%).

2. Dissolve the 944 g of ester (I) in about 6 liters of chloroform. Add a solution of 907 g of bromine in about 1.8 liters of chloroform. After the addition, which requires several hours, reflux the reaction medium for 2 hours and then concentrate the solution until the appearance of crystals of bromo-ester. Cool and allow to crystallize, centrifuge and dry the crystals in a stove under vacuum. In this way there are obtained 1250 g of methyl p-bromo-orthocresotate (II) (yield 90%).

Melting point: 109°C.
Thin-layer chromatography: a single spot.

3. Saturate 3.7 liters of absolute methanol with 750 g of ammonia and add the above 1250 g of bromo-ester.

Heat and maintain the temperature at 50°–60°C for 3 hours.

The maximum pressure recorded within the autoclave is about 6 kg/cm². After elimination of the excess ammonia under vacuum, concentrate to dryness, wash the solid with water, and recrystallize from 25 liters of benzene.

1 kg of pure p-bromo-ortho-cresotamide is obtained. (yield of the amidation: 85%).

METHOD B
(Reaction of Acetylated Acid Chloride on the Corresponding Amine)

Basic reaction:

PRODUCT C          PRODUCT D          PRODUCT E

The product is in the form of white crystals; it is soluble in alcohol, methyl pyrrolidone, propylene glycol and ether; it is insoluble in water and petroleum ether.

Melting point: 173°C.
Plate Chromatography:
Support: Kiesel Gel F 254
Solvent: ethyl acetate/petroleum ether (50:50)
$R_f$: 0.46

Another example:
1. Dissolve 956 g of ortho-cresotic acid in 4 liters of acetone. Add 567 g of NaHCO₃ and then add thereto 835 g of dimethyl sulfate. After refluxing for 5 hours, cool, filter off the salt which has formed, and concentrate to dryness. Subject the crude ester thus obtained The intermediate acetyl derivatives can be isolated or saponified to lead directly to the amides desired.

1 mol of acid chloride (Product C) is added in separate portions to a chloroform solution of an amine mol.

The reaction mixture is refluxed for several hours; the solvent is distilled.

The residual product is recovered by the customary techniques.

The deacetylation is effected by treating Product D with a 1N aqueous soda solution.

The following derivatives have been obtained by Method A as intermediates capable of undergoing further aminolysis:

Methyl 5-chloro-ortho-cresotate
   (R' = OCH₃, X = Cl)
Overall formula: C₉ H₉ Cl NO₃
White crystals — melting point: 62°C.
Silica plate chromatography.
Solvent: ethyl acetate/petroleum ether 35:60
$R_f$: 0.48 (U.V. development)
Insoluble in water and propylene glycol;
2% soluble in ethanol and 8% soluble in DMF.
Methyl 5-iodo-ortho-cresotate
   (R' = OCH₃, X = I)

Overall formula: $C_9 H_9 IO_3$
White crystals — melting point: 97°C.
Silica plate chromatography.
Solvent: ethyl acetate/petroleum ether 35:60
$R_f$: 0.51 (U.V. development)
Insoluble in water and propylene glycol;
2% soluble in ethanol and 10% soluble in DMF.
Methyl 5-nitro-ortho-cresotate
   ($R' = OCH_3$, $X = NO_2$)
Overall formula: $C_9 H_9 NO_5$
Yellow needles — melting point: 126°C.
Silica plate chromatography
Solvent: petroleum ether/ethyl acetate 95:5
$R_f$ : 0.60 (U.V. development)
Insoluble in water and propylene glycol.
Very slightly soluble in ethanol (0.5%).

By aminolysis of the methyl esters, a few examples of which have just been given, there have been obtained the following derivatives with amide function other than the 5-bromo 2-hydroxy 3-methyl benzamide described previously;

1. N(dimethyl N',N'-amino 2'-ethyl) 5-bromo-ortho-cresotamide hydrochloride:

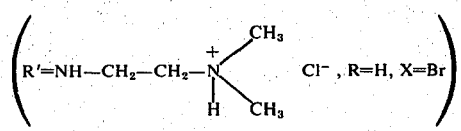

Overall formula: $C_{12} H_{18} Br Cl N_2O_2$
White crystals — melting point = 192°C.
Silica plate chromatography.
Solvent: Butanol/acetic acid/water 6:2:2
$R_f$ = 0.72 (U.V. development)
Soluble in water (10%), ethanol (2%) and propylene glycol (4%).

2. N(diethyl-N',N'-amino 3'-propyl) 5-bromo-ortho-cresotamide hydrochloride:

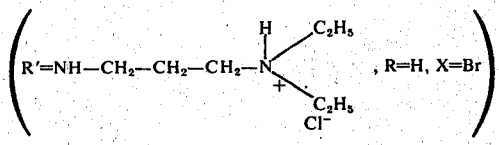

Overall formula: $C_{15} H_{24} Cl Br N_2O_2$
White crystals — melting point: 130°C.
Silica plate chromatography.
Solvent: butanol/acetic acid/water 6:2:2
$R_f$: 0.70 (U.V. development)
2% soluble in water, 8% in ethanol, and 30% in methyl pyrrolidone.

3. N(dimethyl N',N'-amino-3'-propyl) 5-bromo-ortho-cresotamide hydrochloride:

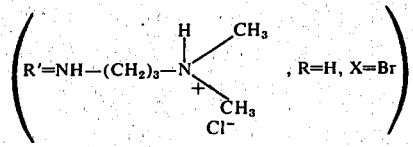

Overall formula: $C_{13} H_{20} Br Cl N_2 O_2$
White crystals — melting point: 203°C.
Silica plate chromatography.
Solvent: butanol/acetic acid/water 6:2:2
$R_f$ : 0.66 (U.V. development)
Soluble in water, practically insoluble in ethanol.

4. N(dimethyl-N',N'-amino 2'-ethyl)5-bromo-ortho-cresotamide hydrochloride:

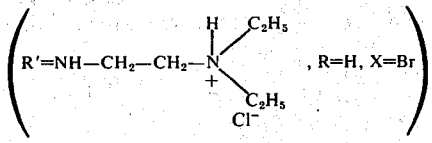

Overall formula: $C_{14} H_{22} Br Cl N_2 O_2$
White crystals — melting point: 132°C.
Silica plate chromatography.
Solvent: butanol/acetic acid/water 6:2:2
$R_f$ : 0.72 (U.V. development)
Soluble in water, 6% soluble in ethanol and 9% soluble in ethylene glycol.

5. N(morpholino 3'-propyl) 5-bromo-ortho-cresotamide hydrochloride:

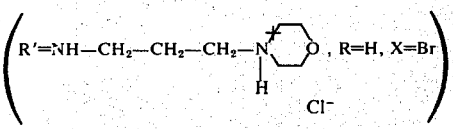

Overall formula: $C_{15} H_{22} Br Cl N_2 O_3$
Pale yellow crystals, melting point: 174°C.
Silica plate chromatography.
Solvent: butanol/acetic acid/water 6:2:2
$R_f$ = 0.80 (U.V. development)
0.3% soluble in water, 6% in ethanol and 7% in propylene glycol.

6. N(morpholino 2'-ethyl) 5-bromo-ortho-cresotamide hydrochloride:

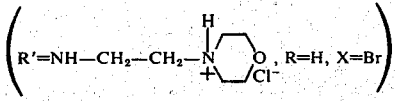

Overall formula: $C_{14} H_{20} Br Cl N_2 O_3$
White crystals — melting point: 228°C.
Silica plate chromatography.
Solvent: butanol/acetic acid/water 6:2:2
$R_f$ = 0.82 (U.V. development)
0.5% soluble in water, 0.3% in ethanol and 1% in DMF.

7. N(pyrrolidino 2'-ethyl) 5-bromo-ortho-cresotamide hydrochloride:

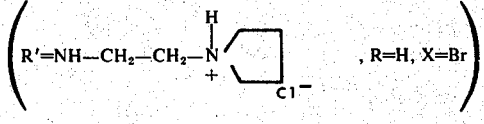

Overall formula: $C_{14} H_{20} Br Cl N_2 O_2$
White crystals — melting point: 184°C.
Silica plate chromatography.
Solvent: butanol/acetic acid/water 6:2:2
$R_f$ = 0.75 (U.V. development)
10% soluble in water, 3% in ethanol, and 7% in propylene glycol.

8. 5-chloro-ortho-cresotamide:
   ($R' = -NH_2$, $R = H$, $X = Cl$)
Overall formula: $C_8 H_8 Cl NO_2$
White crystals — melting point: 181°C.
Silica plate chromatography.
Solvent: ethyl acetate/petroleum ether 30:70

$R_f = 0.55$ (U.V. development)

5% soluble in ethanol, 1% in propylene glycol, 20% in dimethyl acetamide, and 15% in methyl pyrrolidone. Insoluble in water.

9. 5-iodo-ortho-cresotamide:
(R' = —NH$_2$, R = H, X = I)

Overall formula: $C_8 H_8 INO_2$
Beige crystals, melting point: 180°C.
Silica plate chromatography.
Solvent: ethyl acetate/petroleum ether 30:70
$R_f = 0.60$ (U.V. development)

Insoluble in water, 9% soluble in ethanol, 50% in dimethyl formamide, and 25% in dimethyl acetamide.

10. 5-nitro-ortho-cresotamide
(R' = NH$_2$, R = H, X = NO$_2$)

Overall formula: $C_8 H_8 O_4 N_2$
Orangeish-white crystals — melting point: 245°C.
Silica plate chromatography.
Solvent: ethyl acetate/petroleum ether 25:75
$R_f = 0.41$ (U.V. development)

20% soluble in dimethyl formamide, 6% in dimethyl acetamide, 12% in methyl pyrrolidone, and 0.5% in propylene glycol.
Insoluble in water and in ethanol.

11. N(methyl) 5-bromo-ortho-cresotamide:
(R' = NH — CH$_3$, R = H, X = Br)

Overall formula: $C_9 H_{10} Br NO_2$
White crystals — melting point: 162°C.
Silica plate chromatography.
Solvent: ethyl acetate/petroleum ether 30:70
$R_f = 0.76$ (U.V. development).

12. N(ethyl) 5-bromo-ortho-cresotamide:
(R' = NH — C$_2$H$_5$, R = H, X = Br)

Overall formula: $C_{10} H_{12} Br NO_2$
White crystals — melting point: 82°C.
Silica plate chromatography.
Solvent: ethyl acetate/petroleum ether 10:90
$R_f = 0.63$ (U.V. development).

13. N(butyl) 5-bromo-ortho-cresotamide
(R' — NH — CH$_2$—CH$_2$—CH$_2$—CH$_3$, R = H, X = Br)

Overall formula: $C_{12} H_{16} Br NO_2$
White crystals — melting point: 76°C.
Silica plate chromatography.
Solvent: ethyl acetate/petroleum ether 5:95
$R_f = 0.41$ (U.V. development).

14. N(isobutyl) 5-bromo-ortho-cresotamide

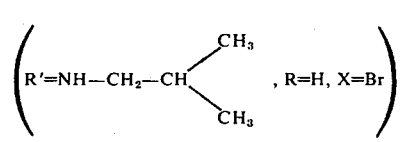

Overall formula: $C_{12} H_{16} Br NO_2$
White crystals — melting point: 67°C.
Silica plate chromatogrphy.
Solvent: ethyl acetate/petroleum ether 5:95
$R_f = 0.40$ (U.V. development).

15. 5-bromo-meta-cresotamide (the methyl is in 4 position):
(R' = NH$_2$, R = H, X = Br)

Overall formula: $C_8 H_8 Br NO_2$
White crystals — melting point: 239°C.
Silica plate chromatography.
Solvent: ethyl acetate/petroleum ether 25:75
$R_f = 0.39$ (U.V. development)

The following derivatives, indicated by way of illlustration and not of limitation, were synthesized by Method B (reaction between acetylated acid chloride and the corresponding amine):

1. N(phenyl) 5-bromo-ortho-cresotamide

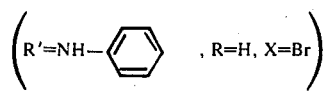

Overall formula: $C_{14} H_{12} Br NO_2$
Orange crystals — melting point: 128°C.
Silica plate chromatography.
Solvent: ethyl acetate/petroleum ether 5:95.
$R_f = 0.48$ (U.V. development)

2. N(cyclohexyl) 5-bromo-ortho-cresotamide

Overall formula: $C_{14} H_{18} NO_2$
Beige crystals — melting point: 150°C.
Silica plate chromatography.
Solvent: ethyl acetate/petroleum ether 5:95.
$R_f = 0.50$ (U.V. development).

3. N,N-diethyl, 5-bromo-ortho-cresotamide

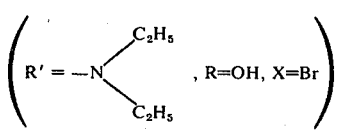

Overall formula: $C_{12} H_{16} Br NO_2$
White crystals — melting point: 77°C.
Silica plate chromatography
Solvent: ethyl acetate/petroleum ether 30:70
$R_f$: 0.67 (U.V. development).

4. N,N'-diisopropyl 5-bromo-ortho-cresotamide

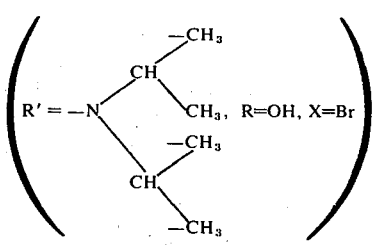

Overall formula: $C_{14} H_{20} Br NO_2$
Pink crystals — melting point: 147°C.
Silica plate chromatography.
Solvent: ethyl acetate/petroleum ether 5:95
$R_f$: 0.28 (U.V. development)

The O-acetylated derivatives serving as intermediaries in Method B can also be obtained from the amides claimed by treatment with acetic anhydride.

Thus it was possible to synthesize the following derivative:

O-acetyl N,N-diethyl 5-bromo-ortho-cresotamide

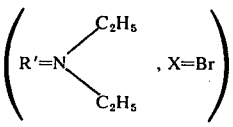

Overall formula: $C_{14} H_{18} Br NO_3$
White crystals — melting point: 90°C.

Silica plate chromatography.
Solvent: ethyl acetate/petroleum ether 50:50.
$R_f$ : 0.53 (U.V. development).

The applicant was also able to test new derivatives satisfying the general formula, which derivatives are obtained from the etherification of the phenol function.

The preparation and physical-chemical characteristics of a derivative with ether function is given below by way of illustration but not of limitation:

O-allyl 5-bromo ortho-cresotamide

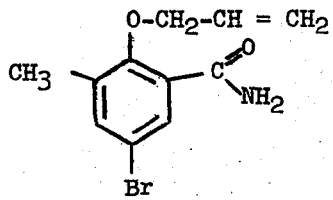

($R' = NH_2$, $R = CH_2 — CH = CH_2$, $X = Br$)

Preparation:

1 mol of 5-bromo ortho-cresotamide is added to a methanolic solution of 1.2 mol of sodium; it dissolves immediately; thereupon 2 mol of allyl chloride are added drop by drop, reflux is effected for several hours, and evaporation to dryness is then effected.

The residue is treated with ether/water, the ether phase is washed with an aqueous solution of 1N soda and then with water until neutral; it is concentrated and crystallized by the addition of petroleum ether.

The white crystals obtained have a melting point of 147°C.

Overall formula: $C_{11} H_{12} Br NO_2$

Silica plate chromatography.
Solvent: ethyl acetate/petroleum ether 30:70.
$R_f$ : 0.41 (U.V. development).

Among the O-acyloylated derivatives, the applicant has more particularly studied methyl 2-(α-thenoyloxy) 3-methyl 5-bromo benzoate.

($R$ = thenoyl Radical $R' = OCH_3$, $X = Br$)

To 6 g of methyl 5-bromo 2-hydroxy 3-methyl benzoate add 4 g of thenoyl chloride in the presence of 6 g of pyridine; there is obtained, in a yield of 93%, crystals of methyl 2-(α-thenoyloxy) 3-methyl 5-bromo benzoate which are soluble in acetone, chloroform, ether and methanol and insoluble in water, propylene glycol and glycerol.

Melting point: 88°C.

The acute toxicity of these new derivatives is rather low; it has been determined as follows on mice (method of Miller and Tainter):

methyl 5-bromo 2-hydroxy 3-methyl benzoate
$DL_{50}$/per os = about 1.600 mg/kg
5-bromo 2-hydroxy 3-methyl benzamide
$DL_{50}$/per os = about 7.800 mg/kg
5-bromo 2-hydroxy 3-methyl benzamide
$DL_{50}$/I.P. = about 1.500 mg/kg
2-hydroxy 3-methyl benzamide
$DL_{50}$/I.P. = about 700 mg/kg
N (dimethyl N',N'-amino 3'-propyl) 5-bromo-ortho-cresotamide hydrochloride
$DL_{50}$/I.P. = about 316 mg/kg
N (diethyl N',N'-amino 2'-ethyl) 5-bromo-ortho-cresotamide hydrochloride
$DL_{50}$ I.P. = about 178 mg/kg
N (morpholino 3'-propyl) 5-bromo-ortho-cresotamide hydrochloride
$DL_{50}$/I.P. = about 237 mg/kg
N (morpholino 2'-ethyl) 5-bromo-ortho-cresotamide hydrochloride
$DL_{50}$/I.P. = 562 mg/kg
N (pyrrolidino 2'-ethyl) 5-bromo-ortho-cresotamide hydrochloride
$DL_{50}$/I.P. = 178 mg/kg
5-chloro ortho-cresotamide
$DL_{50}$/I.P. = 560 mg/kg
methyl 5-chloro ortho-cresotate
$DL_{50}$/I.P. = 178 mg/kg
methyl 5-iodo ortho-cresotate
$DL_{50}$ I.P. = 750 mg/kg
methyl 5-nitro ortho-cresotate
$DL_{50}$ I.P. = 178 mg/kg The pharmacological properties of the new derivatives which are the object of the present description have been studied. During their primary pharmacological screening these various substances showed a definite power as depressant of the central nervous system — sedative, muscular-relaxant and anticonvulsant properties and an anti-pyretic activity. Substantial musculolytic and choleretic properties have also been found. Finally all these derivatives have very definitely potentialized the antalgic power of derivatives such as aspirin, noramidopyrine and even morphine.

POTENTIALIZATION OF BARBITURATE NARCOSIS (MICE)

a. Technique:

Evaluation of the increase of the duration of the sleep induced by 60 mg/kg of mebubarbital (I.P.) (N = 10 mice).

b. Carrying Out of the Test:
$t_o$ → oral administration of the compound.
$t_o + 60'$ → injection of sodium mebubarbital and determination of the periods of narcosis.

c. Results Obtained: (Percentage of increase in the duration of the sleep).

| COMPOUNDS | mg/kg | % increase |
|---|---|---|
| N (dimethyl N,N'-amino 2'-ethyl) 5-bromo ortho-cresotamide | 100 | + 78% |
| N (diethyl N,N'-amino 3'-propyl) 5-bromo ortho-cresotamide | 50 | + 72% |
|  | 100 | + 130% |
| N (dimethyl N,N'-amino 3'-propyl) 5-bromo ortho-cresotamide | 100 | + 80% |
| N (diethyl N,N'-amino 2'-ethyl) 5-bromo ortho-cresotamide | 100 | + 102% |
| methyl 2 (α-thenoyloxy) 3-methyl 5-bromo benzoate | 100 | + 75% |
| N (morpholino 3'-propyl) 5-bromo ortho-cresotamide | 100 | + 100% |
| N (pyrrolidino 2'-ethyl) 5-bromo orthocresotamide | 100 | + 100% |
| 5-chloro ortho-cresotamide | 50 | + 70% |
|  | 100 | + 140% |
| methyl 5-chloro ortho-cresotate | 100 | + 92% |
| methyl 5-iodo ortho-cresotate | 100 | + 90% |
| methyl 5-nitro ortho-cresotate | 100 | + 60% |
| O-acetyl N,N-diethyl 5-bromo ortho-cresotamide | 100 | + 40% |
| 5-bromo meta-cresotamide | 100 | + 120% |
| methyl 5-bromo ortho-cresotate | 100 | + 97% |
| 5-bromo ortho-cresotamide | 30 | + 29.8% |
|  | 100 | + 132 % |
|  | 300 | + 134 % |

The new derivatives which are the object of the present invention also potentialize the sleep induced by chloral hydrate. With respect to anticonvulsive activity (convulsive attacks induced by pentetrazole), the derivatives whose amide function is not substituted have proven to be of the greatest interest.

Technique:

The compound is injected in the mouse interparenterally 30 minutes before the I.V. injection of 75 mg/kg of pentetrazole.

The number of mice showing tonic convulsions is noted and the percentage mortality determined.

The vehicle is an oil solution; a volume of 0.2 mg/20 g of body weight is administered.

| Results: COMPOUNDS | mg/kg | % protection |
|---|---|---|
| Controls (20 mice) | 0 | 0 |
| Mephenesine | 100 | 0 |
| N-(dimethyl N,N'-amino 2'-ethyl) 5-bromo ortho-cresotamide | 100 | 25% |
| N (pyrrolidino 2'-ethyl) 5-bromo ortho-cresotamide | 100 | 32% |
| 5-bromo ortho-cresotamide | 100 | 39.5% |
|  | 300 | 49.3% |
| 5-chloro orthocresotamide | 100 | 38% |
|  | 200 | 44% |
| Methyl 5-chloro ortho-cresotate | 100 | 22% |
| Methyl 5-iodo ortho-cresotate | 100 | 20% |
| Methyl 5-nitro ortho-cresotate | 100 | 10% |
| 5-bromo meta-cresotamide | 100 | 28% |

In view of the homogeneity of this family of new derivatives forming the object of the present patent, the applicant did not deem it necessary, after a prior study of chronic toxicity, to test all the new derivatives in man; however, it selected those which it considered most promising, this manner of procedure, of course, not being of a limitative character.

These derivatives were the subject of clinical tests carried out on volunteers suffering various algias and feverish conditions and, by themselves or associated with other active principles, gave the satisfactory therapeutic results which one had a right to expect.

The formulas of the different drugs containing some of the new derivatives forming the object of this patent are, by way of illustration:

Formula 1

Tablets, according to formula:

| 5-chloro ortho-cresotamide | 300 mg |
|---|---|
| Excipients, q.s.p. | 1 tablet |

Formula 2

Tablets, according to formula:

| 5-chloro ortho-cresotamide | 150 mg |
|---|---|
| Aspirin | 350 mg |
| Excipients, q.s.p. | 1 tablet |

Formula 3

-continued

Suppositories, according to formula:

| N (morpholino 2'-ethyl) 5-bromo ortho-cresotamide hydrochloride | 200 mg |
|---|---|
| Promethazine | 1 mg |
| Excipient, q.s.p. | 1 suppository |

Formula 4

Injectable ampoules (intramuscular), according to the formula

| 5-bromo meta-cresotamide | 100 mg |
|---|---|
| Neutralized oil excipient, q.s.p. | 5 ml |

Formula 5

Tablets, according to formula

| 0-allyl 5-bromo ortho-cresotamide | 150 mg |
|---|---|
| Excipient, q.s.p. | 1 tablet |

Formula 6

Tablets, according to formula

| 5-bromo 2-hydroxy 3-methyl benzamide | 250 mg |
|---|---|
| Excipients, q.s.p. | 1 tablet |

Formula 7

Tablets, according to formula

| 5-bromo 2-hydroxy 3-methyl benzamide | 150 mg |
|---|---|
| Acetyl salicylic acid | 350 mg |
| Excipients, q.s.p. | 1 tablet |

Formula 8

Suppositories, according to formula

| 5-bromo 2-hydroxy 3-methyl benzamide | 125, 250 and 500 mg |
|---|---|
| Excipients, q.s.p., 1 suppository, "infants," children, "adults" | |

The present invention also relates to the pharmaceutical forms which can be administered by mouth, rectally, parenterally and locally in which there are associated with the active principles described in the present invention also other active principles which can usefully supplement the therapeutic properties of the new derivatives. An enumeration of these active principles which are widely known and used in therapy could only be limitative.

We claim:

1. A composition useful as an anticonvulsant which comprises an anticonvulsant amount of an N—$C_1$ to $C_4$-alkyl-5-bromo-ortho-cresotamide in a pharmaceutically acceptable diluent.

2. A composition of claim 1 wherein the compound is N-ethyl-5-bromo-ortho-cresotamide.

3. A method of reducing convulsions in a host which comprises administering to the host an anticonvulsant amount of an N—$C_1$ to $C_4$-alkyl-5-bromo-ortho-cresotamide.

4. A method of claim 3 wherein the compound is N-ethyl-5-bromo-ortho-cresotamide.

* * * * *